United States Patent [19]

Uchida et al.

[11] Patent Number: 4,792,527
[45] Date of Patent: Dec. 20, 1988

[54] METHOD OF ASSAYING BIOLOGICALLY ACTIVE SUBSTANCES AND LABELLING AGENTS THEREFOR

[75] Inventors: Takafumi Uchida, Tokyo; Shuntaro Hosaka, Kamakura, both of Japan

[73] Assignee: Toray Industries, Inc., Tokyo, Japan

[21] Appl. No.: 707,171

[22] Filed: Feb. 28, 1985

Related U.S. Application Data

[63] Continuation of Ser. No. 397,080, Jul. 12, 1982, abandoned.

[30] Foreign Application Priority Data

Jul. 17, 1981 [JP] Japan .................. 61-110896
Oct. 6, 1981 [JP] Japan .................. 61-158183

[51] Int. Cl.[4] .......................................... G01N 33/546
[52] U.S. Cl. .................................. 436/507; 436/509; 436/533; 436/534; 436/805; 436/818; 436/821; 436/827; 436/828
[58] Field of Search ............... 436/533, 534, 541, 507, 436/509, 805, 818, 821, 827, 828

[56] References Cited

U.S. PATENT DOCUMENTS

| 3,654,090 | 4/1972 | Schuurs | 435/7 |
| 4,145,406 | 3/1979 | Schick | 436/541 X |
| 4,166,104 | 8/1979 | Wagner | 436/541 X |
| 4,210,723 | 7/1980 | Dorman | 436/534 X |
| 4,226,747 | 10/1980 | Roncari | 436/534 X |
| 4,226,847 | 10/1980 | Ogasa | 436/534 |
| 4,254,096 | 3/1981 | Monthony | 436/534 X |
| 4,305,925 | 12/1981 | Kapmeyer | 436/534 X |
| 4,319,882 | 3/1982 | Sharma | 422/73 X |
| 4,331,649 | 5/1982 | Chantler | 436/534 |
| 4,341,758 | 7/1982 | Sakakibara | 436/534 X |
| 4,362,531 | 12/1982 | de Steenwinkel | 436/534 |

*Primary Examiner*—Sidney Marantz
*Attorney, Agent, or Firm*—Austin R. Miller

[57] ABSTRACT

A method of assaying biologically active substances by the competitive method or by the sandwich technique, characterized in that fine particles having a diameter of 0.03 to 3 $\mu$m are used in the labelling agent.

16 Claims, 7 Drawing Sheets

F I G. I.

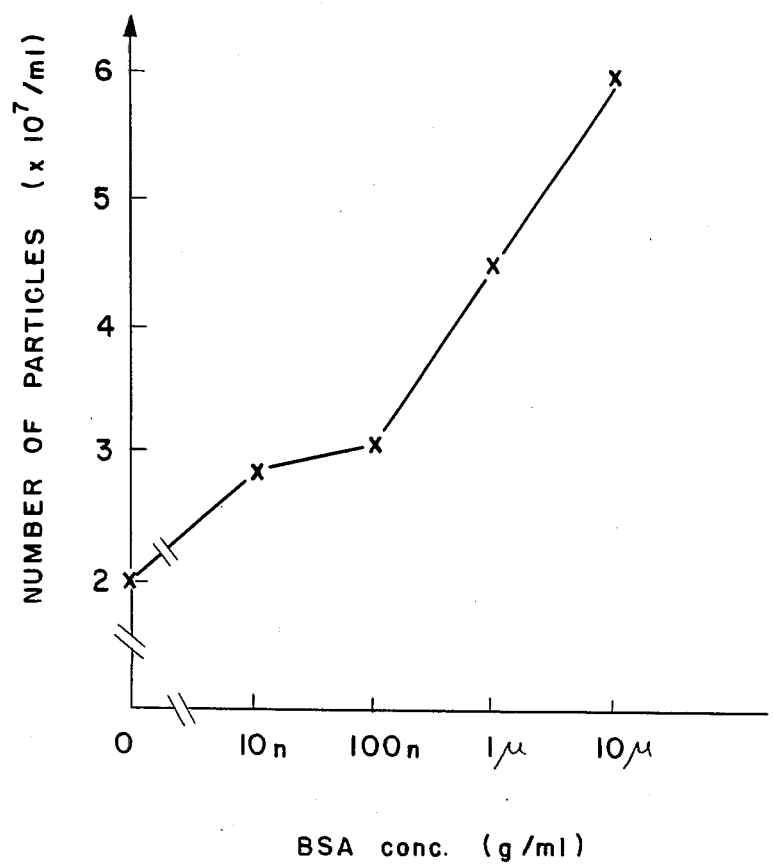
F I G. 2.

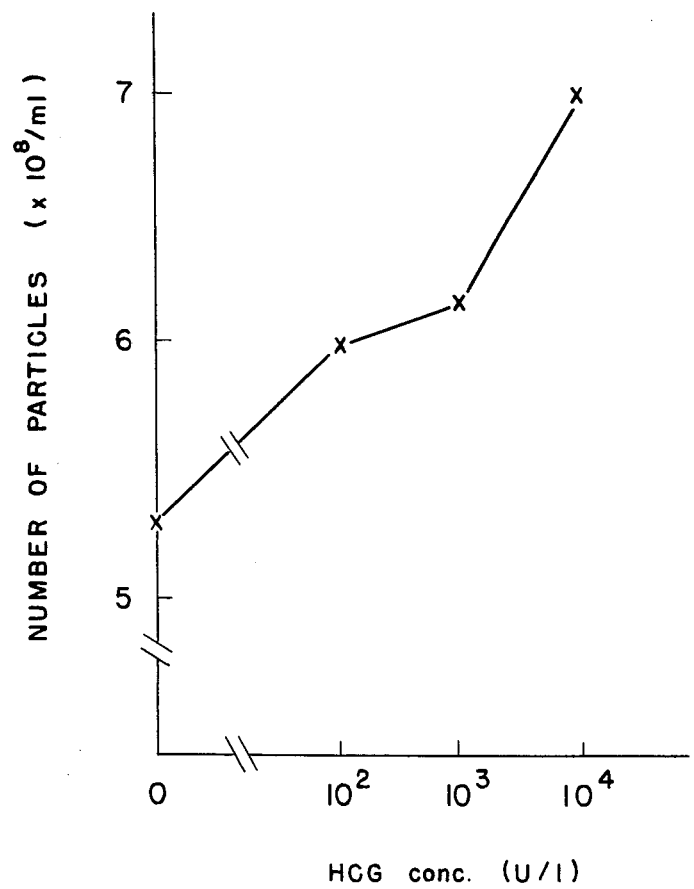
F I G. 3.

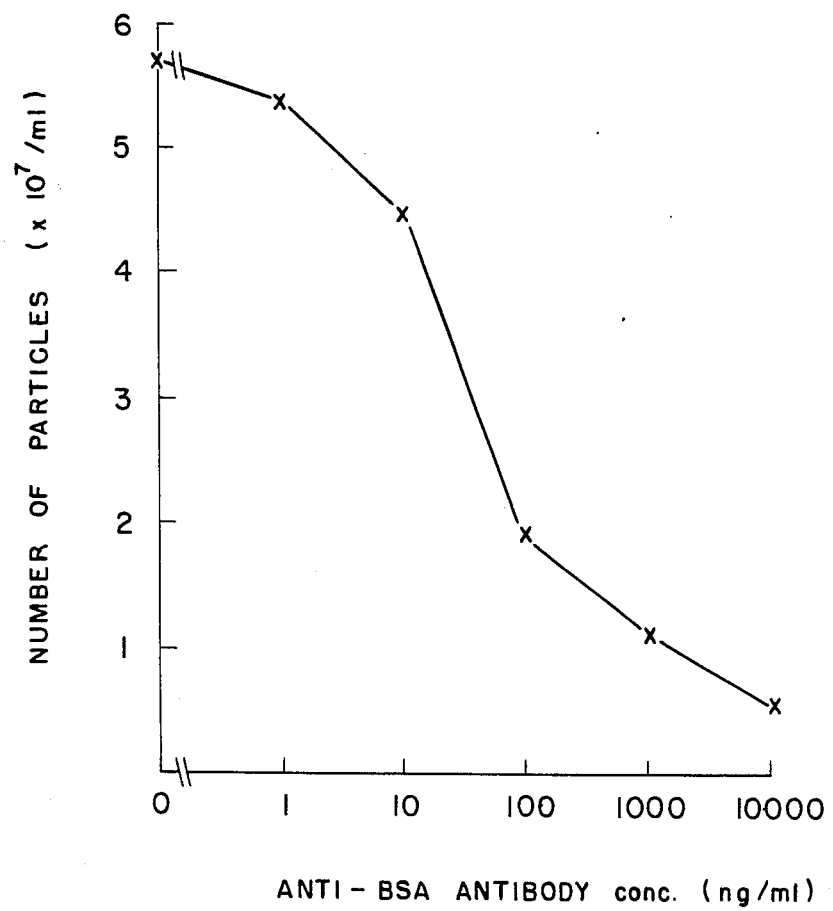
F I G. 4.

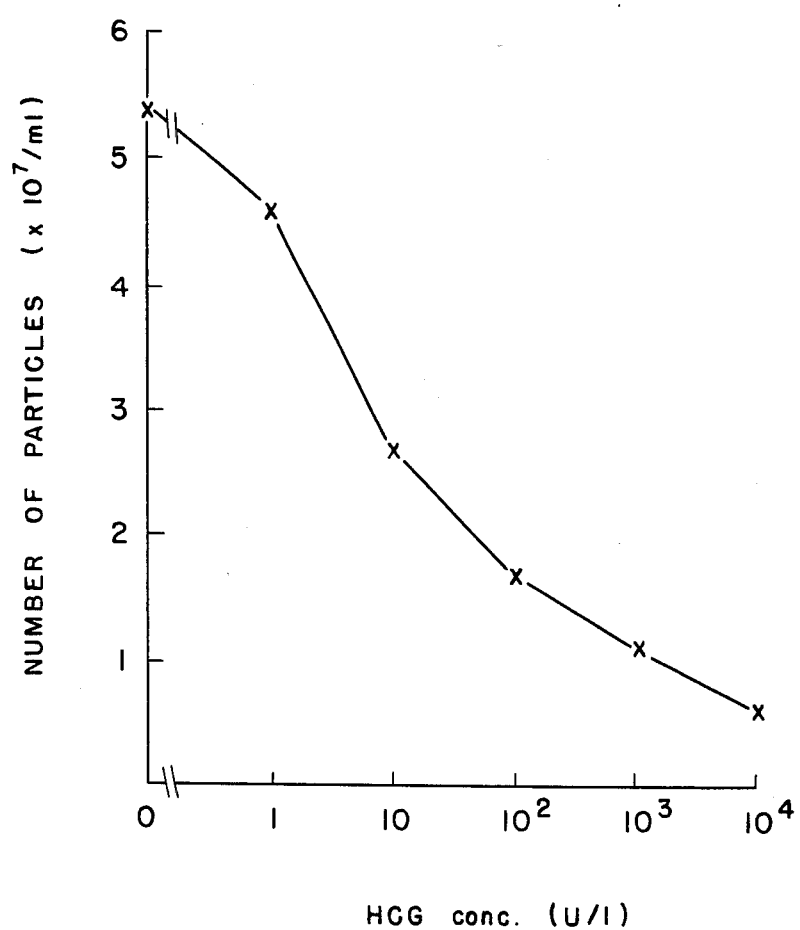
F I G. 5.

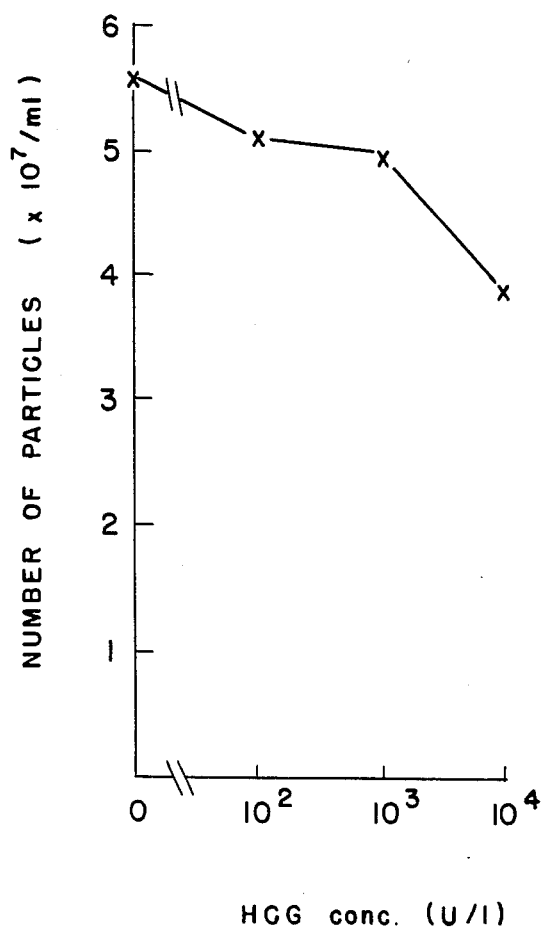
F I G. 6.

METHOD OF ASSAYING BIOLOGICALLY ACTIVE SUBSTANCES AND LABELLING AGENTS THEREFOR

This application is a continuation, of application Ser. No. 397,080, filed 7/12/82, now abandoned.

BACKGROUND OF THE INVENTION

The present invention relates to a method of assaying biologically active substances using fine particles and a labelling agent used therefor.

Recently, methods for the quantitative determination of trace constituents according to antigen-antibody reactions have been employed in clinical laboratory examinations and also in research in the fields of medical science, veterinary science, pharmacy and microbiology.

In classical processes, biologically active substances have been assayed using an erythrocyte agglutination reaction or an immunodiffusion method. Now, there are being developed nephelometric methods wherein an immune complex formed by the antigen-antibody reaction is determined according to the light scattering function of particles suspended in a medium; immunoassay by labelling wherein an antibody or antigen is labelled with a fluorescent dye, a radioisotope or an enzyme and an antigen or antibody is measured; and a method wherein an antigen or antibody is fixed on fine particles of a synthetic polymer and degree of the aggregation of the fine particles caused by the presence of antibody or antigen is observed on a glass plate or microplate or the change in transmittance of light due to the aggregation is measured using a spectrophotometer.

Particularly, radioimmunoassay has been employed broadly as an analytical method having the highest sensitivity. However, this method has serious defects such as the danger of exposure or requiring special installation, since a radioisotope is used. Therefore, the development of an assay method with a high sensitivity to replace radioimmunoassay has been demanded. A method developed under these circumstances is enzyme immunoassay which can be operated easily and has a high sensitivity wherein an enzyme is used in place of the radioisotope and merits of the immunoassay by labelling are maintained. Enzyme immunoassay surely has a measurement sensitivity comparable to that of radioimmunoassay for some substances. However, the high sensitivity is not always exhibited in the measurement of all substances and reagents used in enzyme immunoassay are relatively expensive. Thus, enzyme immunoassay is still inferior to radioimmunoassay.

Generally, immunoassay methods such as radioimmunoassay may be classified into two methods with respect to their principles. One of them is the competitive method and the other is the sandwich technique. In the competitive method, into a sample liquid containing an antigen or antibody as a substance to be assayed is added the same substance of a known concentration which has been labelled with a labelling agent such as a radioisotope, then the corresponding antibody or antigen is mixed and reacted therewith to form an antigen-antibody complex. The complex and free substances which remain after the complex formation contain both labelled and unlabelled substances to be assayed. By measuring the amount of the labelled substance, a quantitative determination of the substances in the sample is effected. The other method, the sandwich technique comprises two steps. A solid phase on which a bonding partner capable of specifically bonding with a substance to be assayed has been fixed is prepared in advance, reacted with the specimen, and then separated from the liquid phase. In the next step, the substance to be assayed on the solid phase is reacted with a labelled bonding substance obtained by labelling a substance specifically reacting with the substance to be assayed using a radioisotope or the like, and the labelled substance in the solid phase or liquid phase is determined to assay the substance.

Thus, the sandwich technique comprises two steps and, in the first step, the substance to be assayed in the sample is specifically reacted with its bonding partner fixed on the solid phase, whereby only the substance to be assayed is bonded with the solid phase and other substances and ions are removed by washing. Therefore, substances other than the substance to be assayed in the sample, i.e., those interfering with the immunological reaction, are not introduced in the second step. Further, by this treatment, concentration of the substance to be assayed in the measurement liquid is also effected. This is advantageous from the viewpoint of measurement sensitivity and accuracy.

On the other hand, the operation of the competitive method is easier than that of the sandwich technique. According to the competitive method, even a substance having only one antigen determinant can be assayed, while in the sandwich technique, such a substance cannot be assayed.

An object of the present invention is to provide a safe, inexpensive, highly sensitive assay method which can be employed in place of the radioimmunoassay.

A further object of the invention is to provide a new, highly sensitive method of assaying a biologically active substance which comprises using fine particles both in the competitive method and in the sandwich technique.

SUMMARY OF THE INVENTION

The present invention provides two methods of assaying biologically active substances. One is the competitive method and the other is the sandwich technique.

The competitive method of the present invention comprises the steps of competitively reacting a biologically active substance to be assayed in a sample solution and a known amount of the same substance which has been labelled with a labelling agent with a solid phase having a bonding partner capable of specifically bonding with the biologically active substance to be assayed fixed thereon and then determining the labelled substance remaining in the liquid phase to assay the biologically active substance, characterized in that fine particles having a diameter of about 0.03 to 3 µm are used as the labelling agent.

The sandwich technique according to the present invention comprises the steps of reacting a biologically active substance to be assayed in a sample solution with a solid phase having a bonding partner capable of specifically bonding with the biologically active substance to be assayed fixed thereon, separating the solid phase from the reaction mixture, reacting the solid phase with a substance (hereinafter referred to as bonding substance) which has the property of specifically bonding with the biologically active substance to be assayed and which has been labelled with a labelling agent and determining the labelled substance remaining in the liquid phase to assay the biologically active substance, characterized in that fine particles having a diameter of 0.03 to 3 μm are used as the labelling agent.

Namely, the present invention is characterized in that, the substance labelled with a radioisotope or enzyme used in the known method is replaced with a substance labelled with fine particles of a diameter of about 0.03 to 3 μm.

BRIEF DESCRIPTION OF THE DRAWINGS

FIGS. 1–7 show the results of measurement made in Examples 1–7, respectively. FIG. 1 shows the results of the insulin determination, FIG. 2 shows those of BSA determination, FIG. 3 shows those of HCG determination, FIG. 4 shows the results of the anti-BSA antibody determination and FIGS. 5–7 show the results of HCG determination.

DETAILED DESCRIPTION OF THE INVENTION

Competitive Method

Figure 1:
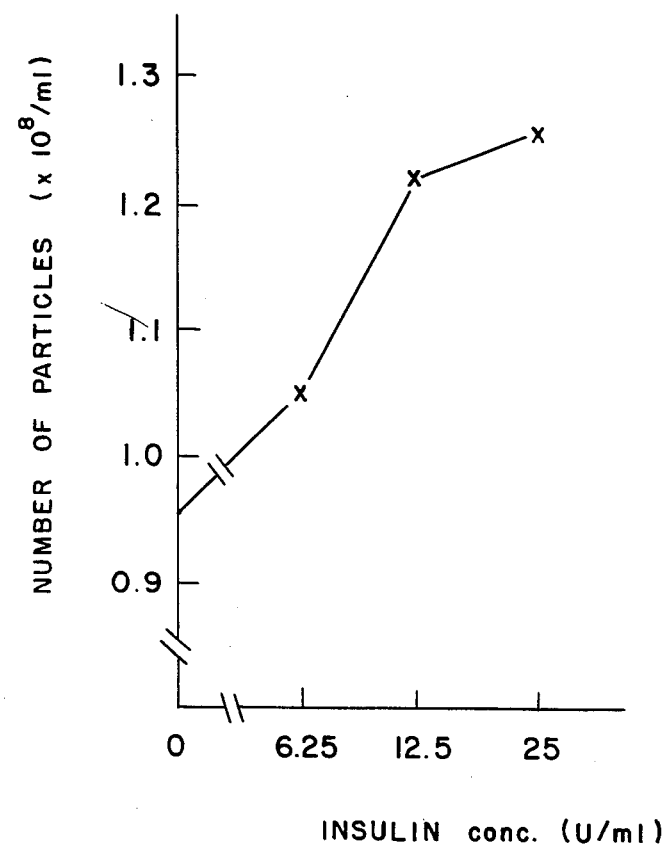

In the competitive method, a given amount of the substance labelled with fine particles (hereinafter referred to as active fine particles (A)) is reacted with a solid phase having a bonding partner fixed thereon concurrently with a specimen or after the reaction of the solid phase with the specimen. The amount of active fine particles (A) bonded with the solid phase is reduced while the amount of active fine particles (A) remaining in the liquid phase is increased as the amount of the substance to be assayed in the sample solution is increased. By counting the number of active fine particles (A) remaining in the liquid phase, the substance to be assayed can be determined quantitatively. The counting can be effected by a method wherein the dispersion of active fine particles (A) is exposed to light and the intensity of scattered light is measured, a method wherein the dispersion of active fine particles (A) is exposed to light and the intensity of transmitted light is measured and a method wherein the number of the active fine particles (A) is counted by means of a particle counter.

Preferably, the solid phase has a shape which permits separation from the active fine particles (A) and is made of a material also separable therefrom. More particularly, the solid phase must be designed so that it can be separated from the active fine particles (A). Separability may be achieved as follows: (1) the solid phase is made in the form of balls or plates far larger than the active fine particles (A) so that they can be picked out from the mixture; (2) when the solid phase is in the form of fine particles, their diameter is made larger than that of the active fine particles (A) so that they can be separated by means of a membrane, filter or centrifugal separator; (3) when the solid phase is in the form of fine particles having a diameter equivalent to that of the active fine particles (A), their specific gravity is made higher than that of the active fine particles (A) so that they can be easily sedimented and separated out by centrifugation; or (4) a magnet-sensitive substance is included in the fine particles of the solid phase so that they can be separated by means of a magnet. The above-specified examples are given only for the purpose of permitting easy understanding of the separation of the solid phase from the active fine particles (A) and they by no means limit the character of solid phase. As materials for the solid phase, stable synthetic organic high molecular weight compounds which can be prepared in an arbitrary form are preferred, although natural polymers and metals are also usable. As such high molecular compounds, there may be mentioned hydrophobic polymers such as polystyrene, polyacrylonitrile, polymethacrylonitrile, polymethyl methacrylate, poly-ε-capramide and polyethylene terephthalate; hydrophilic polymers obtained by cross-linking, e.g., polyacrylamide, polymethacrylamide, poly-N-vinylpyrrolidone, polyvinyl alcohol, poly(2-hydroxyethyl acrylate), poly(2-hydroxyethyl methacrylate), poly(2,3-dihydroxypropyl acrylate), poly(2,3-dihydroxypropyl methacrylate) and polyethylene glycol methacrylate; and copolymers having both hydrophilic and hydrophobic components. A preferred form of the solid phase is fine particles or filaments having a large surface area, while the solid phase may be in the form of plates, test tubes or microplates.

The bonding partner may be fixed on the solid phase by physical adsorption or chemical bonding. For example, protein can be fixed on a hydrophobic solid phase by the physical adsorption; a substance having a carboxyl or amino group can be fixed on a solid phase having an amino or carboxyl group as a functional group via a covalent bond using a carbodiimide; an amino group-containing substance can be fixed on an amino group-containing solid phase via a covalent bond using glutaraldehyde; and an amino group-containing substance can be fixed on a hydroxyl group-containing solid phase via a covalent bond using cyanogen bromide. The covalent bond method is superior to the physical adsorption method having a possibility of desorption of a fixed substance, since a deterging liquid containing a surfactant is used in some cases for washing the solid phase.

The bonding partner used in the present invention is a substance capable of specifically bonding with the substance to be assayed. For example, when an antigen, an antibody, a hormone, an antigen-antibody complex, a saccharide, an immunoglobulin, a lymphokine or complement is the substance to be assayed, the bonding partner is an antibody, an antigen, a hormone receptor, a rheumatoid factor, lectin, protein A, a lymphokine receptor or a complement receptor, respectively.

The fine particles working as a carrier for the active fine particles (A) to be reacted with the solid phase competitively with the substance to be assayed preferably have uniform particle size and shape so as to attain a high accuracy in the measurement. From the viewpoint of reaction efficiency, a particle size as small as possible is preferred. More particularly, a particle size of less than 3 μm which facilitates Brownian motion is preferred. However, an excessively small particle size is unsuitable from the viewpoint of operation or measurement. A suitable particle size is thus in the range of about 0.03 to 3 μm, and more particularly in the range of about 0.1 to 0.8 μm.

As for the materials of the fine particles, organic high polymers are preferred for the purpose of obtaining fine particles having a uniform, proper particle size. As such materials, there may be mentioned for example, the same hydrophobic polymers, hydrophilic polymers and polymers having both hydrophilic and hydrophobic properties as those mentioned above. The fine particles of the present invention can be prepared by emulsion polymerization or precipitation polymerization. Such polymerization methods are suitable for obtaining fine particles having uniform particle size and shape. Particularly, emulsion polymerization is suitable for obtaining the intended fine particles having a uniform particle size in the range of about 0.5 to 0.03 μm by controlling emulsifier and monomer concentrations.

The substance to be assayed can be bonded with the fine particles by physical adsorption or chemical bonding. These fine particles should have a high dispersibility and should be bonded with the solid phase via the substance to be assayed. Therefore, fine particles prepared by bonding a substance to be assayed with a hydrophilic organic high molecular weight compound as used in the solid phase by a covalent bond are particularly preferred.

The substances to be assayed according to the present invention are those having a partner having a biologically specific affinity therewith. Concretely, they include, for example, antibodies to bacteria such as streptococcus, staphylococcus, diphtheria bacillus, Salmonella and dysentery bacillus as well as their constituents; antibodies to spirochete such as Treponema pallidum and their constituents; antibodies to mycoplasma and constituents thereof; antibodies to protozoa such as plasmodium malariae and their constituents; antibodies to rickettsia and their constituents; antibodies to virus such as adenovirus and influenza, poliomyelitis, measles, German measles, hepatitis and parotitis virus as well as their constituents; antigens such as polysaccharides, human albumin and ovalbumin as well as antibodies to them; hormones such as insulin, thyroid hormone and chorionic gonadotropin; enzymes such as ribonuclease, creatine phosphokinase and asparaginase; antigens and receptors specific to organs such as kidney cell membrane, liver cell membrane, α-fetoprotein and CEA; connective tissue components such as collagen and amyloid; antigens and receptors of blood cells such as red blood cells and platelets; plasma proteins such as fibrin and plasminogen; pathologic globulins such as rheumatic factor and C-reactive protein; immune complex; and autoantibodies to cell membranes, etc.

After completion of the reaction of the solid phase with the specimen and the active fine particles (A), the active fine particles (A) remaining free from the solid phase are determined. Any method of determination which allows quantitative determination of the fine particles may be employed. One of the methods wherein intensity of light scattered by the fine particles is measured comprises exposing the fine particles to a light of a wave length comparable to a diameter of the fine particles and determining the scattered light having a wave length equal to that of the irradiation light (called Mie scattering). According to this method, a highly sensitive determination is possible.

(2) Sandwich Technique

According to the sandwich technique, the specimen is first reacted with a solid phase having a bonding partner. Then, the solid phase reacted with the specimen is separated from the reaction mixture, followed by reacting it with a bonding substance labelled with a labelling agent (hereinafter referred to as active fine particles (B)). Thus, the active fine particles (B) are bonded with the solid phase via the substance to be assayed in the specimen. If the active fine particles (B) are used in an excessive amount, some of them are not bonded with the solid phase but remain in the form of a dispersion in the liquid phase. By counting the number of the active fine particles (B) remaining in the liquid phase, the substance to be assayed can be determined quantitatively. The counting can be effected by the same method described in the Competitive Method.

The solid phase and the bonding partner used in this Sandwich Technique are the same as those used in the afore-mentioned Competitive Method.

After the separation of the solid phase from the liquid phase, the solid phase is washed. The washing method is selected suitably depending on the character of the solid phase. For example, where the solid phase is test tube or microplate, the liquid can be removed easily by decantation or suction. Where the solid phase is fine particles, they are sedimented by means of a centrifugal separator and the supernatant liquid is removed by suction. Where a magnet-sensitive substance is incorporated in the solid phase, the liquid can be removed by suction while the solid phase is maintained by the attraction of a magnet.

Then, the solid phase, obtained after washing, having only the substances of the object of assay bonded therewith through the bonding partner is reacted with active fine particles (B). The active fine particles (B) comprise fine particles on which, a bonding substance capable of specifically bonding with the substances to be assayed has been fixed. The fine particles are the same as the ones described in the Competitive Method.

The bonding substance herein used is a substance capable of specifically bonding with the substance to be assayed. The bonding substance may be the same as or different from the bonding partner fixed on the solid phase.

For example, in case the substance to be assayed is immunoglobulin, protein A may be used as the bonding partner for bonding the substance to be assayed with the solid phase and anti-immunoglobulin antibody may be used as the bonding substance on the active fine particles or, alternatively, the anti-immunoglobulin antibody may be used as both the bonding partner and substance.

According to this Sandwich Technique, the same substances in the specimen described in the Competitive Method can be assayed.

For quantitative determination of the active fine particles (B) remaining free from the solid phase, the Mie scattering method described above in the Competitive Method is preferably employed.

EXAMPLE 1

DETERMINATION OF INSULIN (Competitive Method)

Preparation of Fine Particles Used as the Solid Phase

Fine particles used as the solid phase were prepared by mixing and polymerizing glycidyl methacrylate, 2-hydroxyethyl methacrylate and triethylene-glycol dimethacrylate in a molar ratio of 85.7:9.5:4.8, aminating the resulting fine particles of the polymer and then hydrolyzing them as described in the specification of Japanese Patent Application No. 43618/1980. Hydrophilic fine particles having an average diameter of 4.3 μm were thus prepared.

Preparation of a Solid Phase Having Anti-swine Insulin Antiserum Fixed Thereon

The aminated and hydrolyzed fine particles were activated with glutaraldehyde according to the method of Japanses Patent Application No. 43618/1980. The thus treated fine particles were dispersed in 0.15 mol/l physiological phosphate buffer saline solution (PBS) of pH 7.2 to obtain a 1% dispersion. The dispersion was mixed with an equal volume of anti-swine insulin antiserum (Miles) and the mixture was allowed to react at 30°

C. for 3 hours. Bovine serum albumin (hereinafter referred to a BSA) was added to the particle dispersion to attain a concentration of 1%. After carrying out the reaction for an additional 1 hour, the fine particles were washed by repeated centrifugation (3000 rpm) and resuspension. The particles were dispersed (1% dispersion) in PBS containing 0.1% of BSA to obtain solid phase fine particles having anti-swine insulin antiserum fixed thereon.

Preparation of Fine Particles Used as Active Fine Particles

Glycidyl methacrylate, methacrylic acid and ethylene glycol dimethacrylate were mixed at a molar ratio of 85:10:5. The mixture was added to an aqueous solution containing 0.1% of sodium dodecylsulfate and 0.01 mol/l of ammonium persulfate. The resulting emulsion having a monomer concentration of 10% (W/V) was allowed to react at 60° C. in argon gas atmosphere for 22 hours. The resulting fine particles were aminated and hydrolyzed in the same manner as in the above-described treatment of the solid phase fine particles to obtain fine particles having a uniform diameter of 0.27 μm.

Preparation of Active Fine Particles Having Insulin Fixed Thereon

Fixation of insulin was effected according to the above-described method of fixing anti-swine insulin antiserum on the solid phase fine particles. That is, a 1% dispersion of fine particles treated with glutaraldehyde was mixed with an equal volume of 40 U/ml of swine insulin (NOVO) solution. After carrying out the reaction at 30° C. for 2 hours, BSA was added to the reaction mixture to attain a concentration of 1%. The reaction was continued at 30° C. for 1 hour. The fine particles were washed by repeated centrifugation (10,000 rpm for 30 min) and resuspension. The particles were dispersed in PBS containing 0.1% of BSA to obtain a dispersion having a particle concentration of 1%. Thus, active fine particles having swine insulin fixed thereon were prepared.

Determination of Insulin

100 μl of 1% dispersion of solid phase fine particles having anti-swine insulin antiserum fixed thereon were added to 100 μl of PBS solution containing 25, 12.5 or 6.25 μU/ml of swine insulin. The mixture was allowed to react at 25° C. for 2 hours. Further, 10 μl of the active fine particles having insulin fixed thereon (0.01% dispersion) were added to the reaction mixture and the reaction was carried out at 25° C. overnight. 2.5 ml of PBS were added to the reaction liquid and the mixture was centrifuged at 3000 rpm for 5 minutes to sediment the solid phase and the active fine particles reacted with the solid phase. The dispersion of fine particles unreacted with the solid phase was obtained as a supernatant. The light-scattering intensity of the dispersion of the active fine particles was measured by irradiation with 400 nm light using an Aminco-Bowman spectrofluorometer. The number of fine particles was determined from the light-scattering intensity according to a previously prepared calibration curve, since the light-scattering intensity was approximately proportional to the number of fine particles. As shown in FIG. 1, insulin can be determined quantitatively in the range of 25 to 6.25 μU/ml.

EXAMPLE 2

DETERMINATION OF BSA (Competitive Method)

Preparation of a Solid Phase Having Anti-BSA Antiserum Fixed Thereon

A 1% dispersion of solid phase fine particles prepared in the same manner as in Example 1 and treated with glutaraldehyde was mixed with an equal volume of anti-BSA antiserum (Miles). They were reacted at 30° C. for 3 hours and then human serum albumin (hereinafter referred to as HSA) was added thereto to attain an HSA concentration in the particle dispersion of 1%. The reaction was continued for an additional 1 hour and then the product was washed by repeated centrifugation (3000 rpm) and resuspension. The product was dispersed in PBS containing 0.1% of HSA to obtain fine particles having anti-BSA antiserum fixed thereon.

Preparation of Active Fine Particles Having BSA Fixed Thereon

BSA was added in an amount of 10 mg/ml to 1% dispersion of active fine particles having a diameter of 0.27 μm prepared in the same manner as in Example 1 and treated with glutaraldehye. The reaction was carried out at 30° C. for 3 hours. After washing by repeated centrifugation (10,000 rpm) and resuspension, the product was dispersed in PBS containing 0.1% of HSA to obtain active fine particles having BSA fixed thereon.

Determination of BSA

100 μl of 1% dispersion of solid phase fine particles having anti-BSA antiserum fixed thereon were added to 90 μl of a PBS solution containing 10 μg/ml, 1 μg/ml, 100 ng/ml or 10 ng/ml of BSA and they were allowed to react at 30° C. for 1 hour. Then, the active fine particles having BSA fixed thereon were added to the reaction mixture and the reaction was carried out at 30° C. overnight. 2.5 ml of PBS were added to the reaction liquid. The active fine particles not bonded with the solid phase were separated from the solid phase and the active fine particles bonded with the solid phase by means of a membrane (Millipore Filter RA) having a pore size of 1.2 μm. Scattered light intensity was measured in the same manner as in Example 1 and the number of the fine particles was determined from the intensity.

The relationship between BSA concentration and intensity of scattered light in the range of BSA 10 μg/ml to 10 ng/ml is shown in FIG. 2.

EXAMPLE 3

Determination of Human Chorionic Gonadotropin (hereinafter referred to as HCG) (Competitive Method)

Preparation of a Solid Phase Having Anti-HOG Antiserum Fixed Thereon

A 1% dispersion of solid phase fine particles prepared in the same manner as in Example 1 and treated with glutaraldehyde was mixed with an equal volume of anti-HCG antiserum (16,000 IU/ml) (Miles). They were reacted at 30° C. for 3 hours and then BSA was added thereto to attain a BSA concentration in the particle dispersion of 1%. The reaction was continued for an additional 1 hour and then the product was washed by repeated centrifugation (3,000 rpm) and resuspension. The product was dispersed in PBS containing 0.1% of BSA to obtain a solid phase having anti-HCG antiserum fixed thereon.

Preparation of Fine Particles Used as Active Fine Particles

Glycidyl methacrylate, ethylene glycol dimethacrylate and sodium sulfopropyl methacrylate were mixed in a molar ratio of 88:10:2. The mixture was added to an solution containing 0.125% of sodium dodecylsulfate and 0.01 mol/l of ammonium persulfate to obtain an emulsion having a monomer concentration of 10% (W/V). After carrying out the reaction at 60° C. for 3 hours in argon gas atmosphere, the resulting fine particles were washed by repeated centrifugation (10,000 rpm) and resuspension. After the amination and hydrolysis carried out in the same manner as in the treatment of the solid phase fine particles, uniform fine particles having a diameter of 0.1 μm were obtained.

Preparation of Active Fine Particles Having HCG Fixed Thereon

HCG was fixed in the same manner as in the fixation of BSA on the solid phase fine particles. That is, 3200 IU/ml HCG (Sigma) solution in PBS was mixed with an equal volume of a 0.1% dispersion of fine particles treated with glutaraldehyde and they were allowed to react at 30° C. for 3 hours. Then, BSA was added thereto to attain a BSA concentration in the particle dispersion of 1%. The reaction was carried out for an additional 1 hour. After washing by repeated centrifugation (15,000 rpm for 30 min) and resuspension, the product was dispersed in PBS containing 0.1% of BSA to obtain active fine particles having HCG fixed thereon.

Determination of HCG

A 1/10-fold dilution series (each 90 μl) of HCG ranging from $10^4$ to $10^2$ U/l was prepared. Each sample was reacted with 50 μl of a 1% dispersion of solid phase fine particles having anti-HCG antiserum fixed thereon and 10 μl of a 0.01% HCG fine particle dispersion at 25° C. overnight in a glass test tube. 2.5 ml of PBS were added to the reaction liquid. The active fine particles remaining not bonded with the solid phase were separated out by means of a membrane in the same manner as in Example 2.

The scattered light intensity was measured and the number of fine particles was determined from the intensity.

The relationship between HCG concentration and intensity of scattered light in the range of HCG 10% to $10^2$ U/l is shown in FIG. 3.

EXAMPLE 4

DETERMINATION OF ANTI-BOVINE SERUM ALBUMIN ANTIBODY (Sandwich Technique)

Preparation of Fine Particles Used as the Solid Phase

Fine particles used as the solid phase were prepared by mixing the polymerizing glycidyl methacrylate, 2-hydroxyethyl methacrylate and triethylene glycol dimethacrylate in a molar ratio of 85.7:9.5:4.8, aminating the resulting fine particles of the polymer and then hydrolyzing them as described in the specification of Japanese Patent Application No. 43618/1980. They were hydrophilic fine particles having an average diameter of 4.3 μm.

Fixation of BSA on Fine Particles Used as Solid Phase

The aminated and hydrolyzed fine particles were activated with glutaraldehyde according to the method of Japanese Patent Application No. 43618/1980. The thus-treated fine particles were dispersed in 0.15 mol/l physiological phosphate buffer saline solution (PBS) of pH 7.2 containing 10 mg/ml of BSA (Miles) to obtain a 1% dispersion. The dispersion was allowed to react at 30° C. for 3 hours. The fine particles were washed by repeated centrifugation (3000 rpm) and resuspension. The particles were dispersed in 0.1% human serum albumin (hereinafter referred to as HSA) solution in PBS to obtain fine particles having BSA fixed thereon.

Preparation of Fine Particles Used for Fixing the Bonding Substance

Glycidyl methacrylate, methacrylic acid and ethyleneglycol dimethacrylate were mixed at a molar ratio of 85:10:5. The mixture was added to an aqueous solution containing 0.1% of sodium dodecylsulfate and 0.01M of ammonium persulfate. The resulting emulsion having a monomer concentration of 10% (W/V) was allowed to react at 60° C. in argon gs atmosphere for 22 hours. The resulting fine particles were aminated and hydrolyzed in the same manner as in the above-described treatment of solid phase fine particles to obtain fine particles having a uniform diameter of 0.27 μM.

Fixation of Anti-Rabbit Immunogloblin G (hereinafter referred to as anti-rabbit Ig G) Antibody on Fine Particles Used for Fixing the Bonding Substance The fine particles were activated with glutaraldehyde according to the above-mentioned method of fixing BSA on the solid phase fine particles. The activated particles were dispsered in PBS in which 1 mg/ml of anti-rabbit IgG antibody (prepared using goat) had been dissolved. After carrying out the reaction at 30° C. for 2 hours, HSA was added to the reaction mixture to attain a concentration of 1%. The reaction was continued at 30° C. for 1 hour. The fine particles were washed by repeated centrifugation (10,000 rpm) and resuspension. The particles were dispersed in PBS containing 0.1% of HSA to obtain a dispersion having a particle concentration of 1%. Thus, fine particles having anti-rabbit IgG antibody fixed thereon were prepared.

Quantitative Determination of Anti-BSA Antibody

50 μl of 1% BSA-fixed solid phase fine particle dispersion were added to 200 μl of PBS solution containing 10 μl/ml, 1 μg/ml, 100 ng/ml 10 ng/ml or 1 ng/ml of anti-BSA antibody prepared by immunizing rabbit with BSA in a glass test tube. The mixture was allowed to react at 37° C. under shaking for 1.5 hours. The particles were washed with PBS by repeated centrifugation (3000 rpm) and resuspension. The solid phase was dispersed in 50 μl of PBS. 25 μl of anti-rabbit IgG antibody-fixed fine particles (0.01% dispersion) was added to the resulting dispersion and the mixture was allowed to react at 30° C. for 2 hours. After standing at 4° C. overnight, 2.5 ml of PBS were added to the reaction mixture. The solid phase fine particles were separated from the anti-rabbit IgG antibody-fixed fine particles by means of a membrane having pores of 1.2 μm diameter. (Millipore Filter RA). The light-scattering intensity of the dispersion of the anti-rabbit IgG antibody-fixed fine particles passed through the membrane was measured by the irradiation with 400 nm light using an Aminco- Bowman spectrofluorometer. The number of fine particles was determined from the light-scattering intensity according to a previously prepared calibration curve, since the light-scattering intensity was approximately proportional to the number of the fine particles. As shown in FIG. 4, anti-BSA antibody can be determined quantitatively in the range of 1 ng/ml to 10 μg/ml.

EXAMPLE 5

DETERMINATION OF HUMAN CHLORIONIC GONADOTROPIN (hereinafter refered to as HCG)(Sandwich Technique)

Fixation of Anti-HCG Antibody On Solid Phase Fine Particles

A 1% dispersion of solid phase fine particles prepared in the same manner as in Example 1 and treated with glutaraldehyde was mixed with an equal volume of anti-HCG antiserum (16,000 IU/ml) [Miles]. They were reacted at 30° C. for 3 hours and then BSA was added thereto to attain a BSA concentration in the particle dispersion of 1%. The reaction was continued for an additional 1 hour and then the product was washed by repeated centrifugation (3,000 rpm) and resuspension. The product was dispersed in PBS containing 0.1% of BSA to obtain anti-HCG antibody-fixed solid phase fine particles.

Fixation of Anti-HCG Antibody on Fine Particles Used for Fixing the Bonding Substance The same fine particles as those used for fixing the bonding substance in Example 1 having a particle size of 0.27 μm were used. The fixation was effected in the same manner as in the fixation of the anti-HCG antiserum on the solid phase fine particles. The particles were washed with PBS by repeated centrifugation (10,000 rpm) and resuspension.

Determination of HCG

A 1/10-fold dilution series (each 90 μl) of HCG ranging from $10^4$ U/l to 1 U/l was prepared. Each sample was reacted with 100 μl of 1% dispersion of anti-HCG antibody-fixed solid phase fine particles at 30° C. under agitation for 2 hours in a glass test tube. The product was washed three times with PBS by centrifugation at 3000 rpm to obtain a solid phase bonded with HCG via anti-HCG antibody. With 100 μl of a 1% dispersion of these solid phase fine particles, 10 μl of 0.02% dispersion of anti-HCG antibody-fixed fine particles (0.27 μm) were mixed in a glass test tube and they were reacted at 30° C. for 2 hours. After completion of the reaction, 2.5 ml of PBS were added to the reaction mixture and the whole was centrifuged at 3,000 rpm for 10 min to sediment the solid phase. The supernatant fine particle dispersion was withdrawn. A scattered light intensity was measured in the same manner as in Example 1 and the number of the fine particles was determined from the intensity.

The relationship between HCG concentration and intensity of scattered light in the range of HCG $10^4$ U/l to 1 U/l is shown in FIG. 5.

EXAMPLE 6

DETERMINATION OF HCG (Sandwich Technique)

Adsorption of Anti-HCG Antibody on Microplates 0.05M Tris-HCl (pH 8.0) wad added to the anti-HCG antiserum used in Example 3 in an equal vouume. 200 μl of the resulting liquid was poured in each well of a polystyrene microplate. After standing at 25° C. for 3 hours, the plates were washed with PBS to obtain anti-HCG antibody-adsorbed microplates.

Reaction of HCG with Solid Phase

150 μl of a PBS solution containing 1% rabbit serum and $10^4$, $10^3$, $10^2$ or 0 U/l of HCG were poured in each well of the microplates coated with anti-HCG antiserum. They were reacted at 25° C. for 3 hours. After completion of the reaction, the product was washed with PBS containing 0.1% Triton X-100 and then washed twice with PBS.

Determination of HCG

The anti-HCG antibody-fixed fine particles used were the same as those used in Example 2 (0.27 μm). 10 μl of a 0.02% fine particle dispersion was placed in each well of the solid phase microplate containing 140 μl of PBS. They were reacted at 25° C. for 3 hours and then left to stand at 4° C. overnight. The fine particle dispersion was sucked from each well by means of a pipette and added to 2.5 ml of PBS. Intensity of light scattered by the fine particles was measured in the same manner as in Example 1. The number of fine particles was determined from the intensity. A calibration curve in the range of HCG $10^4$ to $10^2$ U/l prepared as described above in shown in FIG. 6.

EXAMPLE 7

DETERMINATION OF HCG (Sandwich Technique)

Anti-HCG antibody-bonded fine particles (4 μm) were used as the solid phase. A 1/10-fold dilution series (each 90 μl) of HCG ranging from $10^5$ to U/l was prepared. Each sample was reacted with 100 μl of 1% dispersion of anti-HCG antibody-fixed solid phase fine particles at 25° C. under agitation for 3 hours in a glass test tube. The product was washed three times with PBS by repeated centrifugation (3000 rpm) and resuspension to obtain fine particles bonded with HCG via anti-HCG antibody.

10 μl of a 0.02% dispersion of polystyrene latex (Gestate-Slide "Eiken") having a particle size of about 0.2 μm which had been sensitized with anti-HCG antibody were mixed with 100 μl of the thus-prepared 1% dispersion of solid phase fine particles bonded with HCG via anti-HCG antibody in a glass test tube. They were reacted at 25° C. overnight. After completion of the reaction, 2.5 ml of PBS were added to the reaction mixture and the whole was centrifuged at 3000 rpm for 10 min to sediment the solid phase. The supernatant fine particle dispersion was withdrawn. The scattered light intensity was measured in the same manner as in Example 4. The number of fine particles was determined from the intensity.

Figure 7:
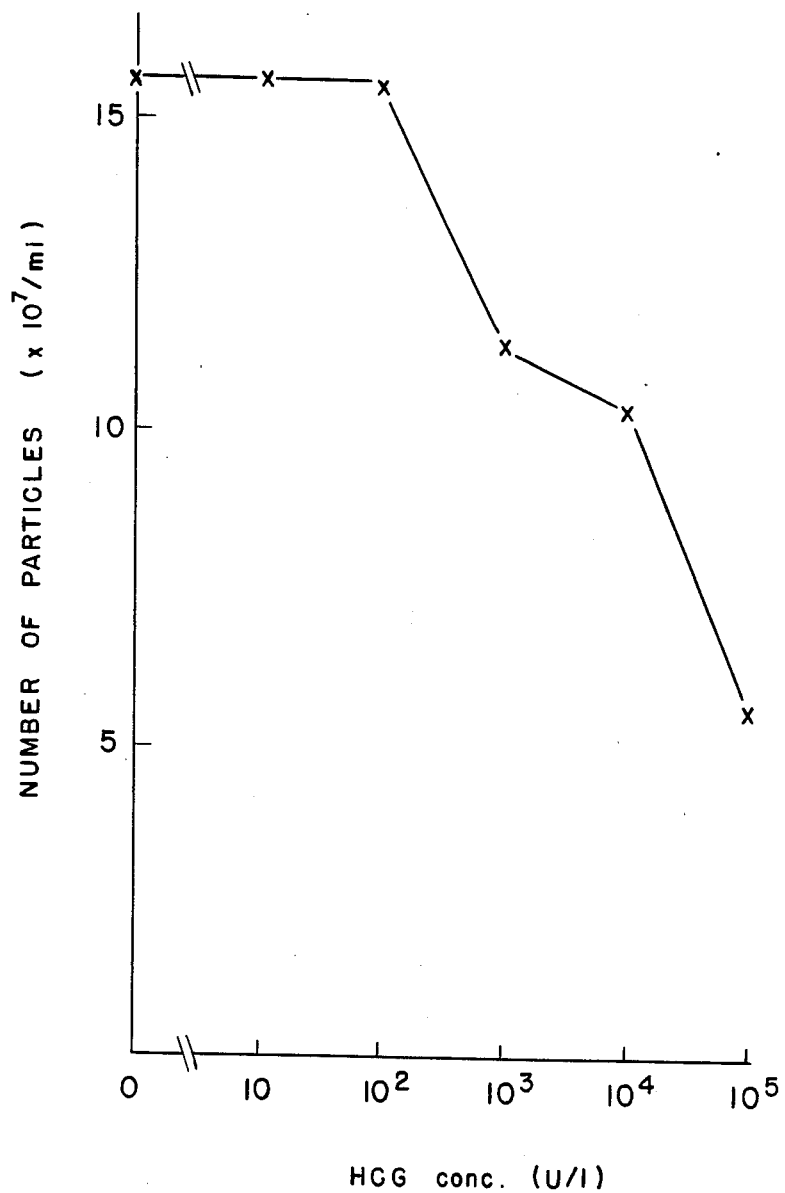

The relationship between the HCG concentration and scattered light intensity in the range of HCG $10^5$ to 10 U/l is shown in FIG. 7.

We claim:

1. A competitive method of assaying a biologically active substance wherein amounts of a biologically active substance to be assayed are previously calibrated against amouts of a labelled biologically active substance remaining in solution by competitively reacting (i) known amounts of an unlabelled biologically active substance, (ii) a predetermined amount of the same biologically active substance labelled with a labelling agent, and (iii) a predetermined amount of a hydrophilic solid phase having fixed thereon a known number of bonding partner(s) capable of specifically bonding with the biologically active substance; separating the hydrophilic solid phase with the labelled and non-labelled substance bonded thereto; and measuring the amounts of labelled biologically active substance remaining in solution comprising the steps of:

a. competitively reacting:
   (i) the biologically active substance to be assayed in a sample solution;
   (ii) the predetermined amount of the same biologically active substance labelled with a labelling agent, the labelling agent comprising hydrophilic fine particles having a diameter of about 0.03–3 μm; and
   (iii) the predetermined amount of the hydrophilic solid phase; and
  b. measuring the amount of labelled biologically active substance remaining in the solution, said amount being quantitatively related to the concentration of said biologically active substance to be assayed.

2. The method as defined in claim 1, wherein the labelled biologically active substance is bonded to the fine particles by chemical bonding.

3. The method as defined in claim 1, wherein the labelled biologically active substance is bonded by a covalent bond to a hydrophilic particle comprising an organic high molecular weight compound.

4. A sandwich method of assaying a biologically active substance with the use of a labelling agent, the labelling agent including hydrophilic fine particles having a diameter of about 0.03 to 3 μm, comprising the steps of:

a. reacting in a solution:
   (i) the biologically active substance to be assayed; and
   (ii) an amount of a hydrophilic solidm phase, the amount of the hydrophilic solid phase being in excess of the amount needed to bond all of the biologically active substance (i), the hydrophilic solid phase being separable from the hydrophilic fine particles, the hydrophilic solid phase having fixed thereon a bonding partner capable of specifically bonding with the biologically active substance to be assayed;
  b. separating the hydrophilic solid phase, with the biologically active substance bonded thereto, from the solution;
  c. reacting the separated hydrophilic solid phase with a known excess amount of a labelled substance which has the property of specifically bonding with said biologically active substance to be assayed and which has been labelled with said labelling agent, to form a sandwich structure and thereby ensuring that a portion of the labelled substance remains unbonded to the biologically active substance; and
  d. measuring the amount of labelled substance remaining in the solution after step (c) in order to assay the biologically active substance.

5. The method as defined in claim 1 or 4, wherein the measuring step includes exposing a dispersion of said labelled substance to light and measuring the intensity of scattered light.

6. The method as defined in claim 1 or 4, wherein the measuring step includes counting the number of particles of said labelled substance by means of a particle counter.

7. The method as defined in claim 1 or 4, wherein the hydrophilic solid phase is a member of the group consisting of stable, synthetic organic high molecular weight compounds, natural polymers and metals.

8. The method as defined in claim 7, wherein the high molecular weight compounds are selected from hydrophilic polymers.

9. The method as defined in claim 8, wherein the hydrophilic polymers are selected from the group consisting of polyacrylamide, polymethacrylamide, poly-N-vinylpyrrolidone, polyvinyl alcohol, poly(2-hydroxyethyl acrylate), poly (2-hydroxyethyl methacrylate), poly (2,3-dihydroxypropyl acrylate), poly(2,3-dihydroxyproyl methacrylate), and polyethylene glycol methacrylate.

10. The method as defined in claim 8, wherein said hydrophilic polymers are prepared by polymerization of glycidyl methacrylate, 2-hydroxyethyl methacrylate and triethyleneglycol dimethacrylate.

11. The method as defined in claim 1 or 4, wherein the bonding partner is selected from the group consisting of an antibody, an antigen, a hormone receptor, a rheumatoid factor, lectin, protein A, a lymphokine receptor and a complement receptor when said substance to be assayed is selected from the group consisting of an antigen, an antibody, a hormone, an antigen-antibody complexd, a saccharide, an immunoglobulin, a lymphokine and a complement, respectively.

12. The method as defined in claim 1 or 4, wherein the hydrophilic fine particles have a diameter of aobut 0.1 to 0.8 μm.

13. The method as defined in claim 1 or 4, wherein the hydrophilic fine particles comprise stable, synthetic organic high molecular weight compounds.

14. The method as defined in claim 13, wherein the high molecular weight compounds are selected from hydrophilic polymers.

15. The method as defined in claim 14, wherein the hydrophilic polymers are selected from the group consisting of polyacrylamide, polymethylacrylamide, ppoly-N-vinylpyrrolidone, polyvinyl alcohol, poly(2-hydroxyethyl acrylate), poly(2-hydroxyethyl methacrylate), poly(2,3-dihydroxypropyl acrylate), poly(2,3-dihydroxypropyl methacrylate), and polyethylene glycol methacrylate.

16. The method as defined in claim 14, wherein said hydrophilic polymers are prepared by polymerization of glycidyl methacrylate, methacrylic acid and ethyleneglycol dimethacrylate, or by polymerization of glycidyl methacrylate, ethyleneglycol dimethyacrylate and sodium sulfopropyl methacrylate.

* * * * *